United States Patent
Nakatani et al.

(10) Patent No.: US 6,709,153 B2
(45) Date of Patent: Mar. 23, 2004

(54) THERMOGRAVIMETRY APPARATUS

(75) Inventors: Rintaro Nakatani, Chiba (JP); Keiko Ooshiro, Chiba (JP); Masafumi Take, Chiba (JP); Ryoichi Kinoshita, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/267,366

(22) Filed: Oct. 9, 2002

(65) Prior Publication Data

US 2003/0086471 A1 May 8, 2003

(30) Foreign Application Priority Data

Oct. 23, 2001 (JP) ........................................ 2001-325227

(51) Int. Cl.[7] .............................................. G01N 25/00
(52) U.S. Cl. ............................. 374/14; 374/10; 374/45
(58) Field of Search ............................... 374/14, 10, 12, 374/45; 177/150, 245

(56) References Cited

U.S. PATENT DOCUMENTS

| 3,902,354 A | * 9/1975 | Harlan et al. ................ 73/15 B |
| 4,802,541 A | * 2/1989 | Bator et al. .................. 177/212 |
| 5,165,792 A | * 11/1992 | Crowe et al. .................. 374/10 |
| 5,370,457 A | * 12/1994 | Iizuka ........................... 374/51 |
| 5,826,983 A | * 10/1998 | Nakamura et al. ............. 374/14 |
| 6,113,261 A | * 9/2000 | Blaine .......................... 374/14 |
| 6,146,013 A | * 11/2000 | Huetter et al. ................ 374/46 |
| 6,347,884 B1 | * 2/2002 | Faure et al. ................... 374/45 |
| 6,354,732 B1 | * 3/2002 | Casati et al. .................. 374/14 |

FOREIGN PATENT DOCUMENTS

| JP | 57061919 A | * 4/1982 | ................ 177/185 |
| JP | 403285154 A | * 12/1991 | ................ 374/43 |
| JP | 406221981 A | * 8/1992 | ................ 374/4 |
| JP | 406221982 A | * 8/1994 | ................ 374/14 |

* cited by examiner

*Primary Examiner*—Gail Verbitsky
(74) *Attorney, Agent, or Firm*—Adams & Wilks

(57) ABSTRACT

In order to provide means for suppressing vibration of a balance arm of a thermogravity apparatus when changing a sample at low cost and with a minimal footprint, there is therefore provided a balance arm having a sample holder, a detector for detecting an amount of shift of the balance arm from an equilibrium position, a control circuit for carrying out feedback control towards the equilibrium position of the balance arm, a driver for driving the balance arm towards the equilibrium position, an exchange stage detector for detecting when a sample is being changed, and a fixed output holding circuit for maintaining the output of the driver at a fixed level while the exchange stage is indicated by the exchange stage detector, wherein output of the driver is fixed during the sample exchange stage.

8 Claims, 1 Drawing Sheet

THERMOGRAVIMETRY APPARATUS

BACKGROUND OF THE INVENTION

The present invention relates to a thermal analysis apparatus, and in particular to thermogravimetry apparatus.

With thermogravimetry apparatus, samples are mounted on a sample holder on top of a plate located at the tip of a balance arm, and the thermogravity apparatus heats the sample using a furnace following a predetermined temperature program. Changes in the weight of the sample are then measured using the balance arm. If there is a change in the weight of the sample the balance arm tilts, moving away from the equilibrium position. The extent of the shifting away from the equilibrium position is electrically detected, and driving is performed so as to return the balance arm to the equilibrium position. The drive force at this point is measured as the change in the weight of the sample. For this reason, feedback control to return to the equilibrium position is always being carried out according to the extent of movement away from the equilibrium position of the balance arm.

When removing or mounting the sample, if a sudden balance arm tilt occurs greater than the response speed of the feedback controls trying to cause the balance arm to return to the equilibrium position, the feedback controls cause a state of oscillation, causing the balance arm to vibrate in a dramatic manner. This vibration can cause samples to be dropped, and balance arm damage etc. Especially when using an automatic sample conveyance apparatus in combination with the thermogravimetry apparatus, although mounting or removal of the sample is carried out with the automatic sample conveyance apparatus in a fixed position, if vibration occurs at this time, problems such as droppage due to failure to grab a sample and collision of the balance arm and the automatic sample conveyance apparatus may occur.

Conventionally, steps have been taken to mechanically fix the balance arm when mounting or removing the sample so as to prevent this type of problem occurring.

The following constraints exist with regards to the implementation of means to mechanically fix the balance arm when mounting the sample.

(1) The fixing means does not become a hindrance to the balance arm when measuring.

(2) The fixing means does not influence measurement precision.

(3) The fixing means can withstand the heat from the furnace or may be retracted to a position where heating may be withstood.

Because of the above constraints, fixing means have become objects containing a large number of moving parts, and tend to also have a large movement range. Such mechanical fixing means are expensive, occupy a large volume, and are an impediment to apparatus price reduction as well as size reduction. In addition, because such equipment contains mechanical moving parts, the likelihood of failure is high.

SUMMARY OF THE INVENTION

The present invention aims to provide a means for fixing and suppressing vibration of the balance arm when mounting or removing samples at a low price, while keeping footprint to a minimum.

The advantage of the present invention is provided with a balance arm having a sample holder, a detector for detecting an amount of shift of the balance arm from an equilibrium position, a control circuit for carrying out feedback control towards the equilibrium position of the balance arm, a driver for driving the balance arm towards the equilibrium position, an exchange stage detector for detecting when a sample is being changed, and a fixed output holding circuit for maintaining the output of the driver at a fixed level while the exchange stage is indicated by the exchange stage detector.

DETAILED DESCRIPTION OF THE INVENTION

Figure 1:
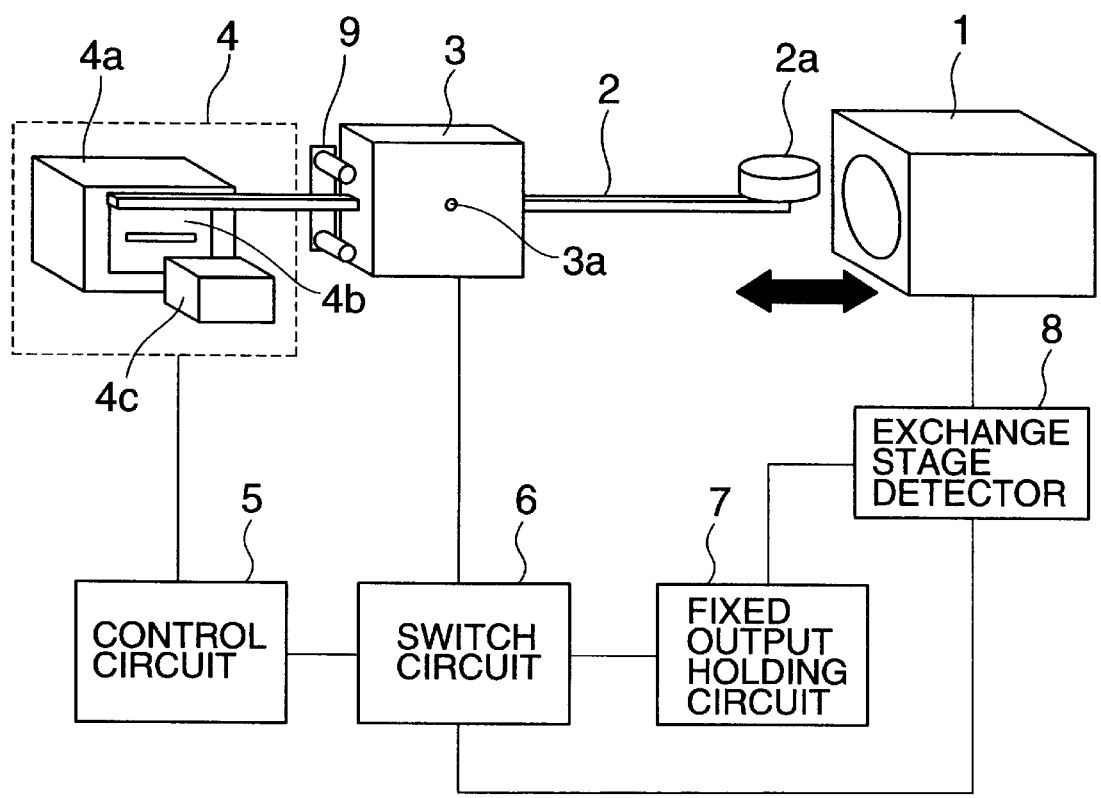
FIG. 1 is a block diagram showing an embodiment of the present invention.

The following is a detailed description of the present invention based on an embodiment.

A furnace 1 in FIG. 1 has the role of heating a sample via a predetermined temperature program. As shown by a broad arrow in FIG. 1, it is possible for furnace 1 to be moved when measuring a sample to a position concealing the sample, and to be moved to a position exposing the sample when changing the sample.

When using an automatic sample conveyance apparatus automatically conveying the sample in combination with a thermogravimetry apparatus, the furnace is moved automatically according to instructions from the automatic sample conveyance apparatus.

A balance arm 2 is provided with a sample holder 2a at one end and is provided with a detector 4 at the other end for detecting shifts in the position of the balance arm and is supported in such a manner as to be freely rotatable by a shaft 3a of a driver 3. In this embodiment, sample holder 2a is fixed in an upward direction at one end of balance arm 2.

A constraint mechanism 9 is a mechanical constraint mechanism for constraining an amount of rotational movement of balance arm 2 rotating taking the shaft 3a as a fulcrum. For example, as shown in the drawings, constraint mechanism 9 is constructed from pin-shaped projections provided at two locations above and below balance arm 2.

Detector 4 comprises a light detector 4a, a slit plate 4b, and a light source 4c. Slit plate 4b having a slit that allows light from light source 4c to pass through is fitted at the other end of balance arm 2. The extent of shifting from the equilibrium position of balance arm 2 can then be detected by detecting light passing through the slit using light detector 4a.

The amount of shifting from the equilibrium position of the balance arm 2 detected at detector 4 is input to a control circuit 5. Control circuit 5 performs feedback control on the driver 3 so as to move balance arm 2 towards the equilibrium position according to the extent of the shifting. Drive force signals for feedback from control circuit 5 are input to the driver 3 via a switching circuit 6.

The driver 3 comprises a coil and a magnet. The coil is integrated with balance arm 2, and is freely rotationally supported at shaft 3a by a torsion band. By passing electric current through the coil according to the drive force signal for the feedback, rotational force of the coil is generated taking the shaft 3a as a fulcrum, thus causing movement towards the equilibrium position of the balance arm 2.

On the other hand, drive force signals input to driver 3 are output from two locations at the control circuit 5 and a fixed output holding circuit 7. When a sample exchange stage is detected at exchange stage detector 8, the drive force signal inputted to driver 3 takes the drive force signal output from the fixed output holding circuit 7 as input via the switching circuit 6. When the sample exchange stage is not detected at the exchange stage detector 8, switching is carried out so as to take the drive force signal output from control circuit 5 as input.

Fixed output holding circuit 7 outputs the drive force signal due to the fixed current, and holds output in such a manner that a fixed rotational force from the driver 3 presses on the balance arm 2. The drive force signals constituting the fixed output may be a positive direction output causing pushing that raises up the end on the sample holder side of the balance arm 2 and a negative direction output pushing so as to push down the end of the balance arm 2 on the side of the sample holder. This embodiment has been conducted so as to have a negative direction output. This is to make it easier to hold the balance arm position fixed when an automatic sample conveyance apparatus mounts the sample from a direction above balance arm 2. This is because the negative fixed output from the fixed output holding circuit 7 will not go lower than the lower limit position of the moveable range as a result of the negative fixed output from the fixed output holding circuit 7 being taken to be a drive signal sufficient to stop the balance arm 2 at the lower limit of the mechanically moveable range using the constraint mechanism 9. On the other hand, when fixed output holding circuit 7 is holding output at a positive fixed output, there is a possible danger that balance arm 2 may descend in a downwards direction if the automatic sample conveyance apparatus applies a greater force than the force pushing balance arm 2 upwards, to push down sample holder 2a.

Exchange stage detector 8 detects a sample exchange stage. When the furnace 1 is in a prescribed position in this embodiment, specifically, a state where sample holder 2 is in an exposed position with respect to furnace 1 is taken to be a sample exchange stage. Exchange stage start is detected when the furnace is moved from the position for the time of measurement, and exchange stage start is detected when sample holder 2 is in an exposed position. When the furnace is moved to the position for during measurement and the sample holder 2 is no longer in an exposed position, the end of the exchange stage is detected.

The following are also possible as a way of sensing the sample exchange stage.

(1) Give notification of the exchange stage from the automatic sample conveyance apparatus.

(2) User gives notification of the exchange stage through a user interface.

The operation during sample mounting is this embodiment is now described.

When mounting samples, the furnace 1 is moved to a position exposing the sample. When furnace 1 has moved to a position exposing sample holder 2, the exchange stage detector 8 detects the start of the sample exchange stage and notifies the fixed output holding circuit 7 and the switching circuit 6 of the fact that the sample exchange stage has commenced. Upon being notified of the sample exchange stage, the fixed output holding circuit 7 continues outputting a fixed output drive force signal pushing the balance arm 2 in a downwards direction.

Upon being notified of the start of the sample exchange stage, the switching circuit 6 cuts the drive force signal from control circuit 5 to driver 3, and transmits a drive force signal from the fixed output holding circuit 7 to the driver 3. Driver 3 then continues pushing down balance arm 2 at a fixed output in a downwards direction, and the position of balance arm 2 becomes fixed.

In this state, during sample exchange using an automatic sample conveyance apparatus, i.e. even when conducting sample mounting or removing, vibration of the balance arm 2 does not occur because feedback controls moving balance arm 2 towards the equilibrium position are not being carried out. In addition, it is possible to carry out sample exchange via an automatic sample conveyance apparatus at a fixed position matching the stop position of balance arm 2, balance arm 2 having been driven at a fixed force by fixed output holding circuit 7, because the balance arm 2 is stopped at the above mentioned mechanical lower movement range limit.

When sample exchange is finished furnace 1 is moved to the measurement time position. Once movement of furnace 1 begins, exchange stage detector 8 detects the end of the sample exchange stage and notifies the fixed output holding circuit 7 and the switching circuit 6. The fixed output holding circuit 7 notified that it is not the sample exchange stage stops output of the drive force signal. Upon being notified that it is not the sample exchange stage, the switching circuit 6 cuts the drive force signal from the fixed output holding circuit 7 to the driver 3, and transmits a drive force signal from control circuit 5 to driver 3. Control circuit 5 takes the amount of displacement of the balance arm 2 from the equilibrium position from the detector 4 as input, and according to the extent of the displacement from the position of equilibrium, goes on to carry out feedback control to return balance arm 2 towards the equilibrium position. Measurements are conducted on the amount of change of the drive force holding balance arm 2 at the equilibrium position, as the sample's weight change amount.

Moreover, a description is given in this embodiment of a horizontal type thermogravimeter example where a sample holder provided at one end of a balance arm is surrounded by a furnace. However, the present invention is by no means limited in this respect and the same results may also be obtained with a vertical type thermogravimeter where a beam is placed in a vertical position at one end of the balance arm, the top end of the beam is provided with a sample holder surrounded by a furnace, with the present invention for a structure provided with the fixed output holding circuit 7 and exchange stage detector 8.

According to the present invention as shown above, by using driver for feedback control to return a balance arm back to an equilibrium position during measurements as means for fixing a balance arm when mounting and removing the sample, and by the realization of means for providing and holding fixed drive force signals to this driver, it has become possible to provide a balance arm fixing means at low cost and a minimal footprint. In particular when using an automatic sample conveyance apparatus in combination with a thermogravimetry apparatus, this is effective as means for fixing a balance arm and preventing vibration of the balance arm when mounting or removing the sample.

What is claimed is:

1. A thermogravimetry apparatus comprising:

a balance arm having a sample holder for mounting samples, a detector for detecting an amount of shift of the balance arm from an equilibrium position, a control circuit for carrying out feedback control towards the equilibrium position of the balance arm based on output from the detector, a driver for driving the balance arm towards the equilibrium position based on output from the control circuit, an exchange stage detector for detecting when a sample is being changed; and a fixed output holding circuit for maintaining the output of the driver at a fixed level, and the output of the driver is being fixed when a sample is changed.

2. The thermogravimetry apparatus of claim 1, wherein the exchange stage detector detects a state of a determined position of a furnace as the sample exchange stage.

3. The thermogravimetry apparatus of claim 1, wherein the fixed output being held by the fixed output holding circuit is a fixed output pushing the above balance arm in a downwards direction.

4. The thermogravimetry apparatus of claim 2, wherein the fixed output being held by the fixed output holding circuit is a fixed output pushing the above balance arm in a downwards direction.

5. The thermogravimetry apparatus of claims 1, further comprising a constraining mechanism for mechanically constraining a range of movement of the balance arm in such a manner that when a fixed output is being outputted to the driver, the balance arm is held at a certain position with the balance arm being constrained by the constraining mechanism.

6. The thermogravimetry apparatus of claims 2, further comprising a constraining mechanism for mechanically constraining a range of movement of the balance arm in such a manner that when a fixed output is being outputted to the driver, the balance arm is held at a certain position with the balance arm being constrained by the constraining mechanism.

7. The thermogravimetry apparatus of claims 3, further comprising a constraining mechanism for mechanically constraining a range of movement of the balance arm in such a manner that when a fixed output is being outputted to the driver, the balance arm is held at a certain position with the balance arm being constrained by the constraining mechanism.

8. The thermogravimetry apparatus of claims 4, further comprising a constraining mechanism for mechanically constraining a range of movement of the balance arm in such a manner that when a fixed output is being outputted to the driver, the balance arm is held at a certain position with the balance arm being constrained by the constraining mechanism.

* * * * *